(12) United States Patent
Lee et al.

(10) Patent No.: US 9,086,406 B2
(45) Date of Patent: Jul. 21, 2015

(54) HEMOGLOBIN A1C-SPECIFIC APTAMER, HEMOGLOBIN-SPECIFIC APTAMER, AND APPLICATIONS THEREOF

(71) Applicant: National Tsing Hua University, Hsinchu (TW)

(72) Inventors: Gwo-Bin Lee, Hsinchu (TW); Shu-Chu Shiesh, Hsinchu (TW); Ching-Chu Wu, Hsinchu (TW); Hsin-I Lin, Hsinchu (TW); Ko-Wei Chang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/225,081

(22) Filed: Mar. 25, 2014

(65) Prior Publication Data

US 2015/0111306 A1    Apr. 23, 2015

(30) Foreign Application Priority Data

Oct. 21, 2013   (TW) .............................. 102137946 A

(51) Int. Cl.
| | |
|---|---|
| C07H 21/02 | (2006.01) |
| C07H 21/04 | (2006.01) |
| C12Q 1/68 | (2006.01) |
| G01N 33/53 | (2006.01) |
| C12N 15/115 | (2010.01) |

(52) U.S. Cl.
CPC .......... *G01N 33/5308* (2013.01); *C12N 15/115* (2013.01); *C12N 2310/16* (2013.01); *G01N 2333/805* (2013.01)

(58) Field of Classification Search
None
See application file for complete search history.

(56) References Cited

U.S. PATENT DOCUMENTS

| | | | |
|---|---|---|---|
| 8,541,561 B2 | 9/2013 | Ban et al. | |
| 8,552,166 B2 | 10/2013 | Tanner et al. | |
| 8,569,252 B2 | 10/2013 | Lee et al. | |
| 2005/0233317 A1* | 10/2005 | Kumar et al. | ..................... 435/5 |
| 2006/0148745 A1* | 7/2006 | Palumbo et al. | ................. 514/44 |
| 2008/0254446 A1* | 10/2008 | Sode et al. | ......................... 435/6 |
| 2015/0024957 A1* | 1/2015 | Cameron et al. | ................. 506/9 |

* cited by examiner

*Primary Examiner* — Richard Schnizer
(74) *Attorney, Agent, or Firm* — WPAT, P.C.; Anthony King

(57) ABSTRACT

The present invention provides a Hemoglobin A1c-specific aptamer and a Hemoglobin-specific aptamer. The aptamers were selected in vitro using SELEX and a microfluidic chip system. The aptamers established low free energy, thus were more stable than conventional antibodies. The high specificity of the aptamers to Hemoglobin A1c or Hemoglobin allows them to be effectively used in diagnosis of diabetes and/or anemia.

9 Claims, 10 Drawing Sheets

SEQUENCE LISTING

```
<160> NUMBER OF SEQ ID NOS: 20

<210> SEQ ID NO 1
<211> LENGTH: 40
<212> TYPE: DNA
<213> ORGANISM: Artificial Sequence
<220> FEATURE:
<223> OTHER INFORMATION: DNA specifically binds to HbA1c

<400> SEQUENCE: 1
acatcgtcgc ggccttagga ggggcggacg ggggggggcg                            40

<210> SEQ ID NO 2
```

```
<211> LENGTH: 40
<212> TYPE: DNA
<213> ORGANISM: Artificial Sequence
<220> FEATURE:
<223> OTHER INFORMATION: DNA specfically binds to HbA1c

<400> SEQUENCE: 2
cgcccccccc cgtccgcccc tcctaaggcc gcgacgatgt                         40

<210> SEQ ID NO 3
<211> LENGTH: 72
<212> TYPE: DNA
<213> ORGANISM: Artificial Sequence
<220> FEATURE:
<223> OTHER INFORMATION: HbA1c-specific aptamer

<400> SEQUENCE: 3
tggcaggaag acaaacacat cgtcgcggcc ttaggagggg cggacggggg ggggcgtggt   60
ctgtggtgct gt                                                      72

<210> SEQ ID NO 4
<211> LENGTH: 72
<212> TYPE: DNA
<213> ORGANISM: Artificial Sequence
<220> FEATURE:
<223> OTHER INFORMATION: HbA1c-specific aptamer

<400> SEQUENCE: 4
acagcaccac agaccacgcc ccccccgtc cgcccctcct aaggccgcga cgatgtgttt    60
gtcttcctgc ca                                                      72

<210> SEQ ID NO 5
<211> LENGTH: 40
<212> TYPE: DNA
<213> ORGANISM: Artificial Sequence
<220> FEATURE:
<223> OTHER INFORMATION: DNA specifically binds to Hb

<400> SEQUENCE: 5
ccaggtgagg gagacgacgc gagtgttaga tggtagctgt                         40

<210> SEQ ID NO 6
<211> LENGTH: 40
<212> TYPE: DNA
<213> ORGANISM: Artificial Sequence
<220> FEATURE:
<223> OTHER INFORMATION: DNA specifically binds to Hb

<400> SEQUENCE: 6
acagctacca tctaacactc gcgtcgtctc cctcacctgg                         40

<210> SEQ ID NO 7
<211> LENGTH: 72
<212> TYPE: DNA
<213> ORGANISM: Artificial Sequence
<220> FEATURE:
<223> OTHER INFORMATION: Hb-specific aptamer

<400> SEQUENCE: 7
ggcaggaaga caaacaccag gtgagggaga cgacgcgagt gttagatggt agctgttggt   60
ctgtggtgct gt                                                      72

<210> SEQ ID NO 8
<211> LENGTH: 72
```

```
<212> TYPE: DNA
<213> ORGANISM: Artificial Sequence
<220> FEATURE:
<223> OTHER INFORMATION: Hb-specific aptamer

<400> SEQUENCE: 8
acagcaccac agaccaacag ctaccatcta acactcgcgt cgtctccctc acctggtgtt    60
tgtcttcctg cc                                                        72

<210> SEQ ID NO 9
<211> LENGTH: 16
<212> TYPE: DNA
<213> ORGANISM: Artificial Sequence
<220> FEATURE:
<223> OTHER INFORMATION: Forward primer of HbA1c-specific aptamer

<400> SEQUENCE: 9
tggcaggaag acaaac                                                    16

<210> SEQ ID NO 10
<211> LENGTH: 16
<212> TYPE: DNA
<213> ORGANISM: Artificial Sequence
<220> FEATURE:
<223> OTHER INFORMATION: Reverse primer of HbA1c-specific aptamer

<400> SEQUENCE: 10
acagcaccac agacca                                                    16

<210> SEQ ID NO 11
<211> LENGTH: 16
<212> TYPE: DNA
<213> ORGANISM: Artificial Sequence
<220> FEATURE:
<223> OTHER INFORMATION: Forward primer of HbA1c-specific aptamer

<400> SEQUENCE: 11
acagcaccac agacca                                                    16

<210> SEQ ID NO 12
<211> LENGTH: 16
<212> TYPE: DNA
<213> ORGANISM: Artificial Sequence
<220> FEATURE:
<223> OTHER INFORMATION: Reverse primer of HbA1c-specific aptamer

<400> SEQUENCE: 12
tggcaggaag acaaac                                                    16

<210> SEQ ID NO 13
<211> LENGTH: 16
<212> TYPE: DNA
<213> ORGANISM: Artificial Sequence
<220> FEATURE:
<223> OTHER INFORMATION: Forward primer of Hb-specific aptamer

<400> SEQUENCE: 13
ggcaggaaga caaaca                                                    16

<210> SEQ ID NO 14
<211> LENGTH: 16
<212> TYPE: DNA
<213> ORGANISM: Artificial Sequence
<220> FEATURE:
<223> OTHER INFORMATION: Reverse primer of Hb-specific aptamer
```

```
<400> SEQUENCE: 14
acagcaccac agacca                                                      16

<210> SEQ ID NO 15
<211> LENGTH: 16
<212> TYPE: DNA
<213> ORGANISM: Artificial Sequence
<220> FEATURE:
<223> OTHER INFORMATION: Forward primer of Hb-specific aptamer

<400> SEQUENCE: 15
acagcaccac agacca                                                      16

<210> SEQ ID NO 16
<211> LENGTH: 16
<212> TYPE: DNA
<213> ORGANISM: Artificial Sequence
<220> FEATURE:
<223> OTHER INFORMATION: Reverse primer of Hb-specific aptamer

<400> SEQUENCE: 16
ggcaggaaga caaaca                                                      16

<210> SEQ ID NO 17
<211> LENGTH: 72
<212> TYPE: DNA
<213> ORGANISM: Artificial Sequence
<220> FEATURE:
<223> OTHER INFORMATION: ssDNA library
<220> FEATURE:
<221> NAME/KEY: misc_feature
<222> LOCATION: (17)..(56)
<223> OTHER INFORMATION: n is a, c, g, or t

<400> SEQUENCE: 17
tggcaggaag acaaacnnnn nnnnnnnnnn nnnnnnnnnn nnnnnnnnnn nnnnnntggt      60
ctgtggtgct gt                                                          72

<210> SEQ ID NO 18
<211> LENGTH: 72
<212> TYPE: DNA
<213> ORGANISM: Artificial Sequence
<220> FEATURE:
<223> OTHER INFORMATION: ssDNA library
<220> FEATURE:
<221> NAME/KEY: misc_feature
<222> LOCATION: (17)..(56)
<223> OTHER INFORMATION: n is a, c, g, or t

<400> SEQUENCE: 18
acagcaccac agaccannnn nnnnnnnnnn nnnnnnnnnn nnnnnnnnnn nnnnnngttt      60
gtcttcctgc ca                                                          72

<210> SEQ ID NO 19
<211> LENGTH: 72
<212> TYPE: DNA
<213> ORGANISM: Artificial Sequence
<220> FEATURE:
<223> OTHER INFORMATION: ssDNA library
<220> FEATURE:
<221> NAME/KEY: misc_feature
<222> LOCATION: (17)..(56)
<223> OTHER INFORMATION: n is a, c, g, or t

<400> SEQUENCE: 19
ggcaggaaga caaacannnn nnnnnnnnnn nnnnnnnnnn nnnnnnnnnn nnnnnntggt      60
```

```
ctgtggtgct gt                                                           72

<210> SEQ ID NO 20
<211> LENGTH: 72
<212> TYPE: DNA
<213> ORGANISM: Artificial Sequence
<220> FEATURE:
<223> OTHER INFORMATION: ssDNA library
<220> FEATURE:
<221> NAME/KEY: misc_feature
<222> LOCATION: (17)..(56)
<223> OTHER INFORMATION: n is a, c, g, or t

<400> SEQUENCE: 20
acagcaccac agaccannnn nnnnnnnnnn nnnnnnnnnn nnnnnnnnnn nnnnnntgtt      60
tgtcttcctg cc                                                           72
```

HEMOGLOBIN A1C-SPECIFIC APTAMER, HEMOGLOBIN-SPECIFIC APTAMER, AND APPLICATIONS THEREOF

CROSS-REFERENCES TO RELATED APPLICATIONS

This application claims priority to Taiwan Patent Application No. 102137946 filed on 21 Oct. 2013. All disclosure of which is incorporated herein by reference in its entirety.

BACKGROUND OF THE INVENTION

1. Field of the Invention

The present invention is related to a hemoglobin A1c-specific aptamer and a hemoglobin-specific aptamer and their applications thereof. 2. The Prior Arts Diabetes mellitus is a non-communicable disease and has gradually become one of the major diseases that threaten people's health in recent years. The etiology of diabetes mellitus is related to the insufficiency or dysfunction of insulin. Insulin is a hormone produced by the pancreas which promotes the entrance of glucose into cells to generate energy and heat; thus, if the human body could not produce enough insulin or the insulin produced was not functioning properly, the blood sugar concentration would maintain in high level since glucose was not able to enter the cells, resulting in diabetes mellitus. According to research, diabetes mellitus is closely related to genetic inheritance and is likely to cause many complications, for example cardiovascular diseases, pneumonitis, neuropathy, chronic kidney diseases, blindness, etc. Diabetes mellitus is also related to some improper lifestyle, hence, is considered to be the most challenging health problem in the $21^{st}$ century.

For treatment of diabetes mellitus, early diagnosis and the control after the disease is diagnosed can reduce the possibility of the occurrence of complications. As a result, it is necessary to develop diabetes-related detections. Currently, the change in blood sugar (fasting and postprandial blood sugar measurements) is commonly used as the diagnosis of treatment of diabetes mellitus as well as the control during treatment. However, blood sugar measurements are likely to be affect by diet, exercise, and insulin, etc, resulting in unstable fluctuation and low accuracy in terms of diagnosis and monitoring. Meanwhile, hemoglobin A1c (HbA1c) can also be used as indicator in the detection of diabetes mellitus since measuring the change of HbA1c reflects the stable state of blood sugar level in approximately 3 months, which is more reliable comparing to measuring blood sugar.

Method for detecting HbA1c nowadays including: Cation exchange HPLC and Boronate Affinity HPLC, etc, however, due to high cost, the requirement of sophisticated equipments, and long processing time, they cannot effectively replace the conventional detection of blood sugar level. Although immunoassay can also be used for the detection of HbA1c, the antibodies used are often expensive. The antibodies themselves are very sensitive to conditions of the surrounding environment such as temperature and moisture, thus, are easy to lose activity and cause inconvenience when transport, store, or use. Furthermore, since antibodies are prepared in batch, activity of antibody is not identical among batches, while errors are likely to occur when operating antibodies due to manual mistakes or effects of the environment of the operation.

Accurate diagnosis and blood sugar control are the foundation of diabetes mellitus treatments, thus a method or product for the detection of HbA1c is needed. However, currently, the market still lacks an accurate, cost-effective, easy-to-store, and highly efficient detecting technique for measuring the level of HbA1c.

SUMMARY OF THE INVENTION

As a result, the present invention provides an aptamer specifically binds to hemoglobin A1c, wherein the aptamer is a nucleic acid molecule comprising at least a nucleic acid sequence of SEQ ID NO: 1 and the complementary nucleic acid sequence thereof, and the complementary nucleic acid sequence is a nucleic acid sequence of SEQ ID NO: 2, wherein when the aptamer comprises the nucleic acid sequence of SEQ ID NO: 1, the aptamer further comprises a forward primer of a nucleic acid sequence of SEQ ID NO: 9, and a reverse primer of a nucleic acid sequence of SEQ ID NO: 10; when the aptamer comprises the nucleic acid sequence of SEQ ID NO: 2, the aptamer further comprises a forward primer of a nucleic acid sequence of SEQ ID NO: 11, and a reverse primer of a nucleic acid sequence of SEQ ID NO: 12.

Another aspect of the present invention is to provide an aptamer specifically binds to hemoglobin, wherein the aptamer is a nucleic acid molecule comprising at least a nucleic acid sequence of SEQ ID NO: 5 and the complementary nucleic acid sequence thereof, said complementary nucleic acid sequence is a nucleic acid sequence of SEQ ID NO: 6; wherein when the aptamer comprises a nucleic acid sequence of SEQ ID NO: 5, the aptamer further comprises a forward primer of a nucleic acid sequence of SEQ ID NO: 13, and a reverse primer of a nucleic acid sequence of SEQ ID NO: 14; when the aptamer comprises the nucleic acid sequence of SEQ ID NO: 6, the aptamer further comprises a forward primer of a nucleic acid sequence of SEQ ID NO: 15, and a reverse primer of a nucleic acid sequence of SEQ ID NO: 16. Besides, the aptamer specifically binds to hemoglobin A1c and/or hemoglobin contains stem-loop secondary structure.

Another aspect of the present invention is to provide a microfluidic chip for detecting the presence of hemoglobin A1c or hemoglobin in blood, comprising at least the aptamer specifically binds to hemoglobin A1c or hemoglobin according to the present invention, for instance the aptamer of SEQ ID. NO: 3 or SEQ ID. NO: 7.

The present invention provides a method for detecting the presence and/or amount of hemoglobin A1c and/or hemoglobin, comprising the steps of: (a) obtaining a sample of bodily fluid from a subject; (b) contacting the sample with at least one aptamer selected from: the group consisting of a nucleic acid sequence of SEQ ID NO: 1, SEQ ID NO: 2, SEQ ID NO: 5 and SEQ ID NO: 6; and (c) detecting the hemoglobin A1c and/or hemoglobin bound to the aptamer of step (b), whereby presence and/or amount of hemoglobin A1c and/or hemoglobin in the sample is determined. If the step (c) is to determine the presence and/or amount of hemoglobin A1c in the sample, the aptamer of SEQ ID NO: 3 comprising hemoglobin A1c-specific nucleic acid sequence of SEQ ID NO: 1 or the aptamer of SEQ ID NO: 4 comprising hemoglobin A1c-specific nucleic acid sequence of SEQ ID NO: 2 is selected; whereas if the step (c) is to determine the presence and/or amount of hemoglobin in the sample, the aptamer of SEQ ID NO: 7 comprising hemoglobin-specific nucleic acid sequence of SEQ ID NO: 5 or the aptamer of SEQ ID NO: 8 comprising hemoglobin-specific nucleic acid sequence of SEQ ID NO: 6 is selected. The determination of the presence and/or amount of hemoglobin A1c and/or hemoglobin in the abovementioned step (c) further comprises binding the hemoglobin A1c and/or hemoglobin with a light emitting reagent, and said light emitting reagent emits luminescence, fluorescence, visible light, or ultraviolet light. In one embodiment of the present invention, the sample is a blood sample.

The hemoglobin A1c-specific aptamer and hemoglobin-specific aptamer of the present invention establish high specificity and binding rate, thus is available for the detection of hemoglobin A1c or hemoglobin in blood. Particularly, the aptamer specific for hemoglobin A1c does not bind to other homologous glycated hemoglobin. Meanwhile, the molecular weight of the aptamer of the present invention is low, and the aptamer also has thermal stability, resist degradation, can be stored for a long period of time, be reusable, and easily attach to other molecules. In comparison with antibody, the aptamer can not only overcome the drawbacks caused by animal production but also be easily synthesized as well as reserve the accuracy of production. Hence, the aptamer of the present invention can substitute the use of antibody for the detection of hemoglobin A1c and hemoglobin in blood with lower cost and higher precision.

The present invention is further explained in the following embodiment illustration and examples. Those examples below should not, however, be considered to limit the scope of the invention, it is contemplated that modifications will readily occur to those skilled in the art, which modifications will be within the spirit of the invention and scope of the appended claims.

DETAILED DESCRIPTION OF THE PREFERRED EMBODIMENT

Figure 1:
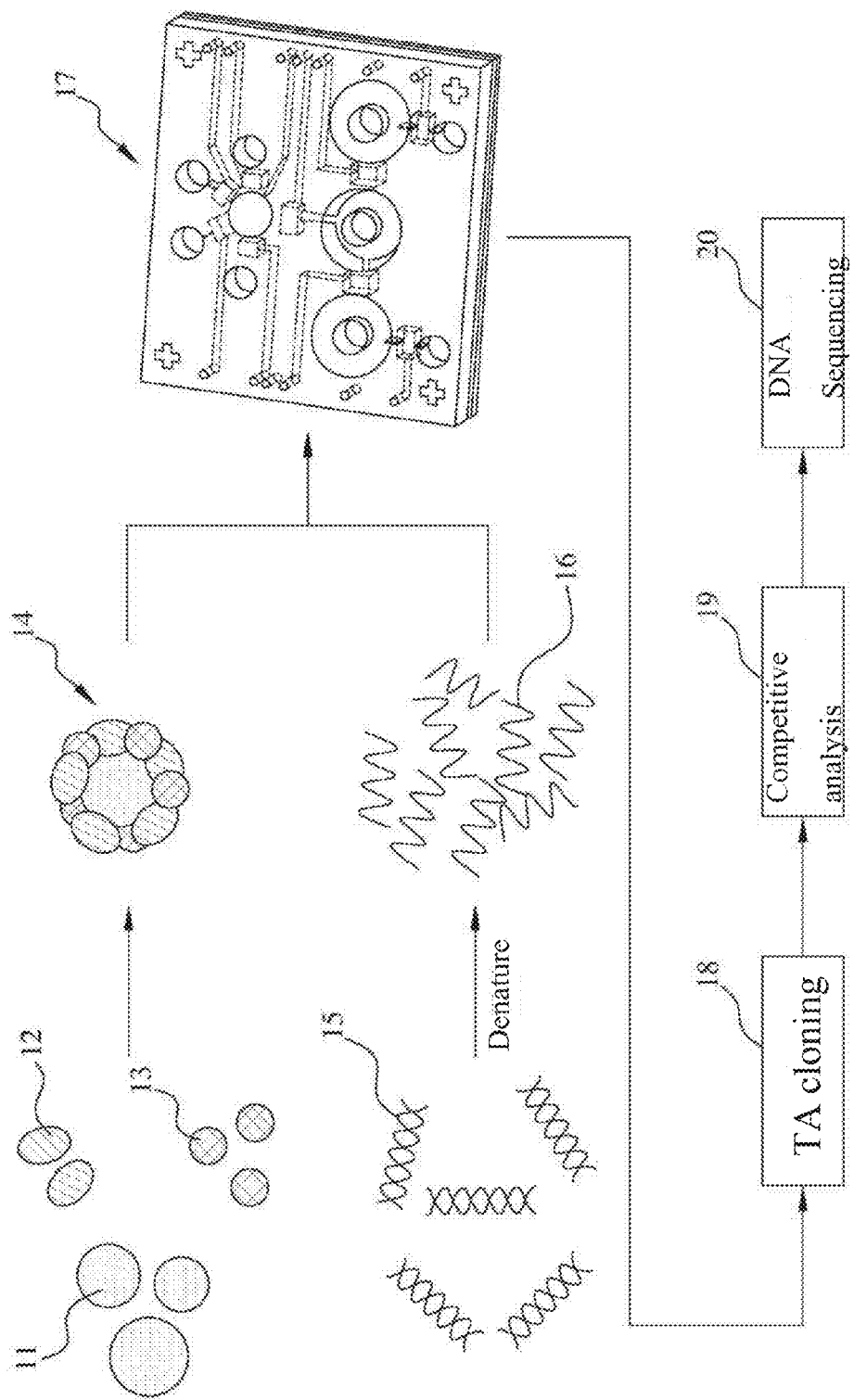
FIG. 1, flow chart for the selection of aptamer specific for hemoglobin A1c or hemoglobin of the present invention.

The hemoglobin A1c-specific aptamer of the present invention was selected by the combination of systematic evolution of ligands by exponential enrichment (SELEX) and microfluidic chip technology. The hemoglobin A1c-specific aptamer of the present invention also establishes high binding rate. Immunological analysis and luminescence detection was further performed using magnetic beads conjugated with hemoglobin A1c-specifc aptamer to verify the high specificity of the aptamer and the feasibility for applying to the detection of hemoglobin A1c in blood or the detection of diabetes mellitus.

The present invention also provides a hemoglobin-specific aptamer which was also obtained via the above SELEX and microfluidic chip. The hemoglobin-specific aptamer of the present invention also establishes high binding rate. Similarly, magnetic beads were conjugated with the hemoglobin-specific aptamer of the present invention and were used to verify its high specificity to hemoglobin using immunological analysis and luminescence detection. Hence, the hemoglobin-specific aptamer is proofed to be effective in the detection of hemoglobin in blood, or anemia.

Definition

As used herein, the terms "polynucleotide", "nucleic acid", "nucleic acid molecule", "nucleic acid sequence", "polynucleotide sequence", and "nucleotide sequence" are interchangeable to refer to polymeric forms of nucleotides of any length. The polynucleotides can comprise deoxyribonucleotides, ribonucleotides, and/or their analogs or derivatives. Examples of structural formations of sequence of polynucleotides also include but not limited to single strand, double strand, stem and loop structure, and the like. Nucleotide sequences shown herein are listed in the 5' to 3' direction.

An aptamer is "specific for" hemoglobin A1c or hemoglobin when the aptamer binds to or interact with hemoglobin A1c or hemoglobin but does not bind to or interact significantly with other forms of hemoglobin or protein.

As used herein, the terms "microfluidic device," "integrated microfluidic device," and "chip," are used interchangeably to refer to a single integral unit that has a microfluidic reactor, one or more microfluidic flow channel(s), and one or more valve(s). Microfluidic devices typically also have other microfluidic components, such as pumps, chamber, mixers, and the like. Most often the chip is fabricated from elastomer, glass, or silicon. Typically, the chip is box-shaped with a height that is relatively small compared to length and width; however, the chip can have other shapes including cubical, cylindrical, and others.

As used herein, the term "antibody" includes but not limited to a polypeptide or a polypeptide fragment substantially encoded by immunoglobin which specifically binds to an analyte (antigen).

Aptamers can be screened by any suitable methods in the art, for example, aptamers can be screened and identified from a random aptamer library by SELEX (systematic evolution of ligands by exponential enrichment). In certain preferred embodiments, aptamers that bind to a cell surface target molecule can be suitably screened and selected by a modified selection method herein referred to as cellSELEX or cellular-SELEX, even if the identity of the cell surface target molecule is unknown. In certain other preferred embodiments, aptamers that bind to a cell surface target molecule can be screened by capillary electrophoresis and enriched by SELEX based on the observation that aptamer-target molecule complexes exhibited retarded migration rate in native polyacrylamide gel electrophoresis as compared to unbound aptamers. The other making and use of aptamers are well known in the art. For example, U.S. Pat. No. 8,552,166 discloses High-affinity nucleic acid aptamers against sclerostin protein; U.S. Pat. No.8,541,561 discloses DNA aptamer, the content of which are all incorporated herein by reference in their entireties. In addition, in certain other preferred embodiments, aptamers can also be synthesized by any suitable methods in the art, for instance, U.S. Pat. No. 8,569,252 discloses nucleolin specific aptamer and use thereof in which the aptamer can be synthesized using synthesizer, the content of which is also incorporated herein by reference in its entirety.

Selex Microfluidic Chip and Detection Microfluidic Chip

Two types of microfluidic chips are provided: a SELEX microfluidic chip and a detection microfluidic chip. The SELEX microfluidic chip is used to automatically perform SELEX for the selection of hemoglobin A1c-specific and hemoglobin-specific aptamers of the present invention, whereas the detection microfluidic chip is applied for the detection of hemoglobin A1c and hemoglobin. Both the SELEX microfluidic chip and the detection microfluidic chip are made of two layers of polydimethylsiloxane (PDMS, Sylgard 184A/B, Dow Corning Corp., USA) and a glass layer (G-Tech Optoelectronics Corp., Taiwan) in a three-layer sandwich structure. Among this three-layer sandwich structure, PDMS layer in the middle is a thin liquid microchannel layer, the upper PDMS layer is a thick air chamber layer, and the bottom layer is a glass layer which serves as a substrate. There are also loading chamber of 5 mm in diameter and microfluidic channels in thickness of 0.3 mm and depth of 0.2 mm A pneumatic component is located at the thick air chamber layer including a micropump, a micromixer, and normally-closed microvalves. The thickness of the thick air chamber layer is approximately 5 mm Air is injected into the thick air chamber layer via one or more than one electromagnetic valves (EMVs) and the EMVs are controlled using computer programs.

Preparation of Hemoglobin A1c-Conjugated Magnetic Beads

For the selection of the hemoglobin A1c-specific aptamer of the present invention via SELEX, hemoglobin A1c-conjugated magnetic beads are further provided according to the following steps:

1. 25 μL of Epoxy-coated magnetic beads (concentration=$4 \times 10^8$ beads/mL, diameter=4.5 μm) were added to an Eppendorf tube.
2. A magnetic filed was applied followed by discarding the supernatant on the top of the Eppendorf tube.
3. 500 μL of PBS (0.01M, pH 7.4) were used to wash the magnetic beads for 3 times.
4. 5 μg of hemoglobin A1c (1 μg/μL, IRMM, IFCC-466) were added to 500 μL of carbonate buffer and incubated at 4° C. overnight.
5. A magnetic filed was again applied followed by discarding the supernatant on the top of the Eppendorf tube and repeating Step 3 above.
6. 500 μL of Tris buffer containing BSA (10 mM Tris, 100 mM NaCl, 2 mM $CaCl_2$, and 1% BSA) were added to the Eppendorf tube to block free spaces on the surface of the hemoglobin A1c-conjugated magnetic beads at 4° C. overnight.

Preparation of hemoglobin-conjugated magnetic beads

Hemoglobin-conjugated magnetic beads are also provided for the selection of hemoglobin-specific aptamer via SELEX, and the preparation thereof is identical to the above preparation process of hemoglobin A1c-conjugated magnetic beads except for the preparation of hemoglobin-conjugated magnetic beads, 5 μL of hemoglobin (2 μg/82 L. Sigma, H0267) were added in Step 4 instead of hemoglobin A1c.

Single Strand DNA (ssDNA) Library

The sequence of the ssDNA library contains: a randomized 40-mer nucleic acid sequence in the center flanked by two 16-mer primers on both ends. Several nucleic acid sequences are included in the ssDNA library. One of the nucleic acid sequences is shown as follow: 5'-TGGCAGGAAGA-CAAAC-N40-TGGTCTG TGGTGCTGT-3'(SEQ ID NO: 17), wherein 5'-TGGCAGGAAGACAAAC -3' (SEQ ID NO: 9) is a Forward primer and 5'-ACAGCACCACAGACCA-3' (SEQ ID NO: 10) is a Reverse primer; another nucleic acid sequence present in the ssDNA library is shown as follow: 5'-ACAGCACCACAGACCA-N40-GTTTGTCTTCCT-GCCA-3'(SEQ ID NO: 18), wherein 5'-ACAGCACCACA-GACCA-3' (SEQ ID NO: 11) is a Forward primer and 5'-TG-GCAGGAAGACAAAC-3' (SEQ ID NO: 12) is a Reverse primer; another nucleic acid sequence present in the ssDNA library is also shown as follow: 5'-GGCAGGAAGA-CAAACA-$N_{40}$-TGGTCTGTGGTGCTGT (SEQ ID NO: 19), wherein 5'-GGCAGGAAGACAAACA-3' (SEQ ID NO: 13) is a Forward primer and 5'-ACAGCACCACAGACCA-3' (SEQ ID NO: 14) is a Reverse primer; another nucleic acid sequence present in the ssDNA library is shown as follow: 5' ACAGCACCACAGACCA-$N_{40}$-TGTTTGTCTTCCTGCC, (SEQ ID NO: 20)wherein 5'ACAGCACCACAGACCA-3' (SEQ ID NO: 15) is a Forward primer and 5'GGCAGGAA-GACAAACA-3' (SEQ ID NO: 16) is a Reverse primer. SELEX was performed to select single strand DNA molecules that show specificity to hemoglobin A1c and/or hemoglobin.

EXAMPLE 1

Selection of Hemoglobin A1c-Specific Aptamer

For the selection of hemoglobin A1c-specific aptamer as substitute for antibody and as a biomarker for the detection of hemoglobin A1c in blood, the present invention utilized magnetic beads techniques and SELELX because only a small amount of reactant is needed and the magnetic beads are capable of withstanding the high temperature during PCR amplification. Hemoglobin A1c and aptamers (nucleic acids) are bound to each other via, primarily, van der Waals interaction and hydrogen bonds. As a result, besides the hemoglobin A1c-specific aptamer, there are also molecules in the ssDNA library that could bind to hemoglobin A1c non-specifically via electrostatic interaction. Hence, a plurality of SELEX cycles was performed to reduce the possibility of selecting non-specific binding molecules.

Please refer to FIG. 1, the flow chart for the selection of aptamer specific for target protein (hemoglobin A1c or hemoglobin) using the microfluidic chip of the present invention. In this embodiment a target protein 12 is hemoglobin A1c. Firstly, according to the above method, the target protein 12 was conjugated with a magnetic bead 11 to form a target protein-magnetic bead complex 14, and the surface of the target protein-magnetic bead complex 14 was further blocked by BSA 13; then, double strand DNA molecules in the ssDNA library 15 were denatured by PCR device to form single strand DNA molecule 16. The target protein-magnetic bead complex 14 and single strand DNA molecule 16 were loaded to a microfluidic chip 17 as mentioned above. The SELEX microfluidic chip 17 can automatically perform processes such as incubation, wash, and amplification for the selection of aptamer with specificity to the target protein 12, which is the hemoglobin A1c-specific aptamer in this embodiment. After a plurality of SELEX cycle, a plurality of single strand DNA molecule is selected. Finally, TA cloning 18 was performed followed by competitive analysis 19 and DNA sequencing 20. The single strand DNA molecule 16 which shows high specificity to hemoglobin A1c is the hemoglobin A1c-specific aptamer of the present invention. In addition, the dissociation constant (Kd) of the hemoglobin A1c-specific aptamer was measured by surface plasmon resonance.

The above SELEX cycle was further described in detail as follow: firstly, PBS was used to elute thin microchannel layer to prevent non-specific binding of single strand DNA molecule to the glass layer. 37 µL of hemoglobin A1c-magnetic bead complex and 3 µL of ssDNA library (10 µM) were loaded to the incubation chamber of the SELEX microfluidic chip and mixed for 5 minutes by the micromixer. After the single strand DNA molecule with high specificity to hemoglobin A1c, also known as aptamer, bound to the hemoglobin A1c-magnetic bead complex, a magnetic filed is applied to retain this aptamer-hemoglobin A1cc-magnetic bead complex inside the incubation chamber. 1000 µL of PBS buffer (0.01M, pH 7.4) were injected by the micropump to wash the unbound or weekly-bound single strand DNA molecules. Then, the single strand DNA molecules that bound to hemoglobin A1c were amplified using PCR by the addition of 28 µL of PCR reagent. The above process of incubation, wash, and amplification is also known as one SELEX cycle. The DNA molecules amplified from the SELEX cycle were denatured prior to proceeding to the next SELEX cycle of incubation, wash, and amplification. The above SELEX selection is a hemoglobin A1c positive selection when hemoglobin A1c-magnetic bead complex was used to bind with single strand DNA molecule, whereas the above SELEX selection is a hemoglobin A1c negative selection when hemoglobin-magnetic bead complex was used. Seven hemoglobin A1c positive selection and hemoglobin A1c negative selection were performed in this embodiment for the selection of hemoglobin A1c-specific aptamer.

The above competitive analysis was further described in detail as follow: the aptamers selected by SELEX were co-incubated with BSA-coated magnetic beads, hemoglobin-conjugated magnetic beads, and hemoglobin A1c-conjugated magnetic beads. Free hemoglobin A1c was then added to serve as competitive group which would compete with the hemoglobin A1c-conjugated magnetic bead for the binding with aptamer. Finally, a magnetic field was applied to capture the aptamer-hemoglobin A1c-magnetic bead complex followed by isolation and PCR amplification of the aptamer.

Figure 2:
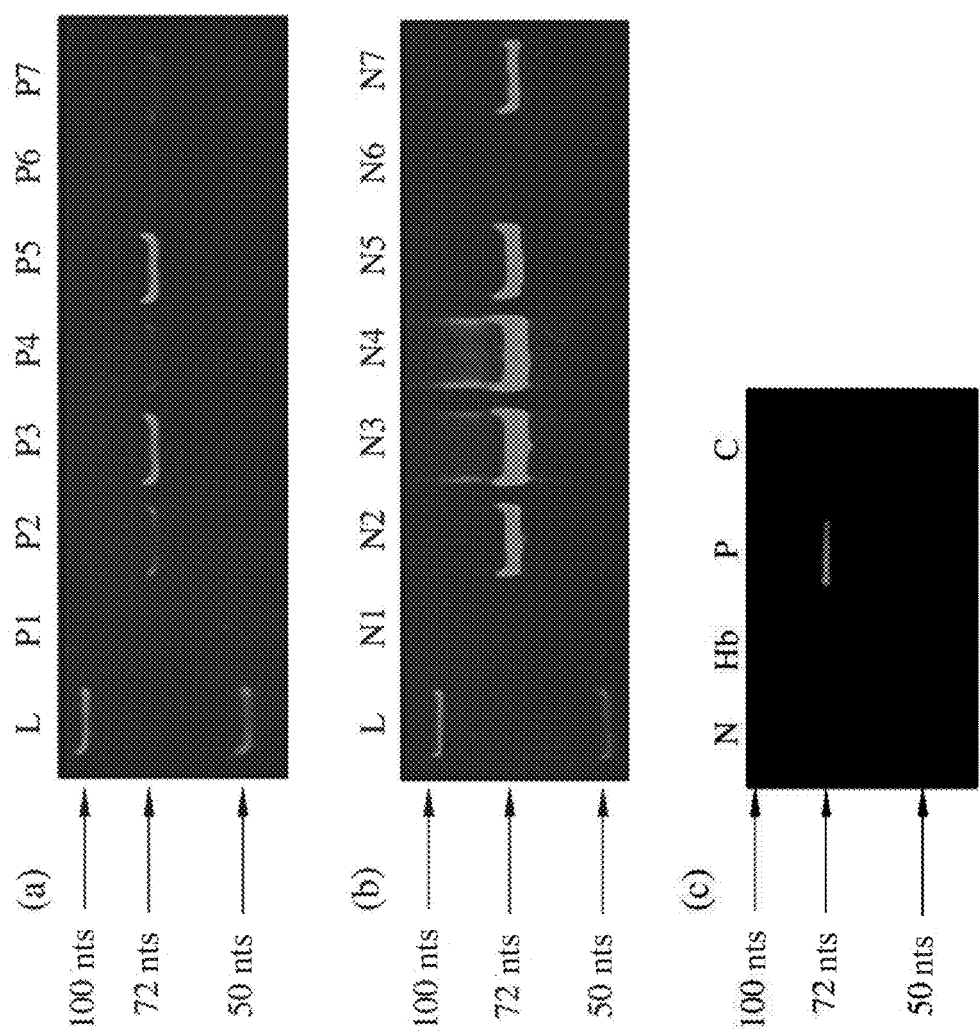
FIG. 2, gel electrophoresis of the selected aptamers of the present invention, wherein (a) represents positive selection; (b) represents negative selection; (c) represents the competitive analysis, wherein N indicates the binding of BSA-conjugated magnetic beads and SEQ ID NO: 3, Hb indicates the binding of hemoglobin-conjugated magnetic beads and SEQ ID NO: 3, P indicates the binding of hemoglobin A1c-conjugated magnetic beads and SEQ ID NO: 3, C indicates the competitive analysis.

Please refer to FIG. 2 for the result of selection of hemoglobin A1c-specific aptamer using SELEX microfluidic chip. As shown clearly in FIGS. 2(a) and 2(b), DNA molecules of 72 nt in length are selected in both hemoglobin A1c positive selection and hemoglobin A1c negative selection, indicating that hemoglobin A1c-specific aptamers are obtained.

The DNA molecules selected were cloned by TA cloning using TOPO vector® system (pCR®2.1-TOPO®, 3.9 kb, Invitrogen Co., USA) and 13 of which were cloned and were further isolated and purified using a commercial kit (Favor-PrepTM Plasmid DNA Extraction Mini Kit, Favorgen Biotech Co., Taiwan), and then were subjected to competitive analysis. The result of competitive analysis is shown in FIG. 2(c), wherein the band of positive control group (hemoglobin A1c, P) is significantly clearer than the band of competitive group (C) indicating that the aptamer of the present invention exhibits high affinity to hemoglobin A1c; the band of positive control group (hemoglobin A1c, P) is clearer than the band of hemoglobin (Hb) indicating that the aptamer of the present invention specifically binds to hemoglobin A1c but not hemoglobin.

Figure 3:
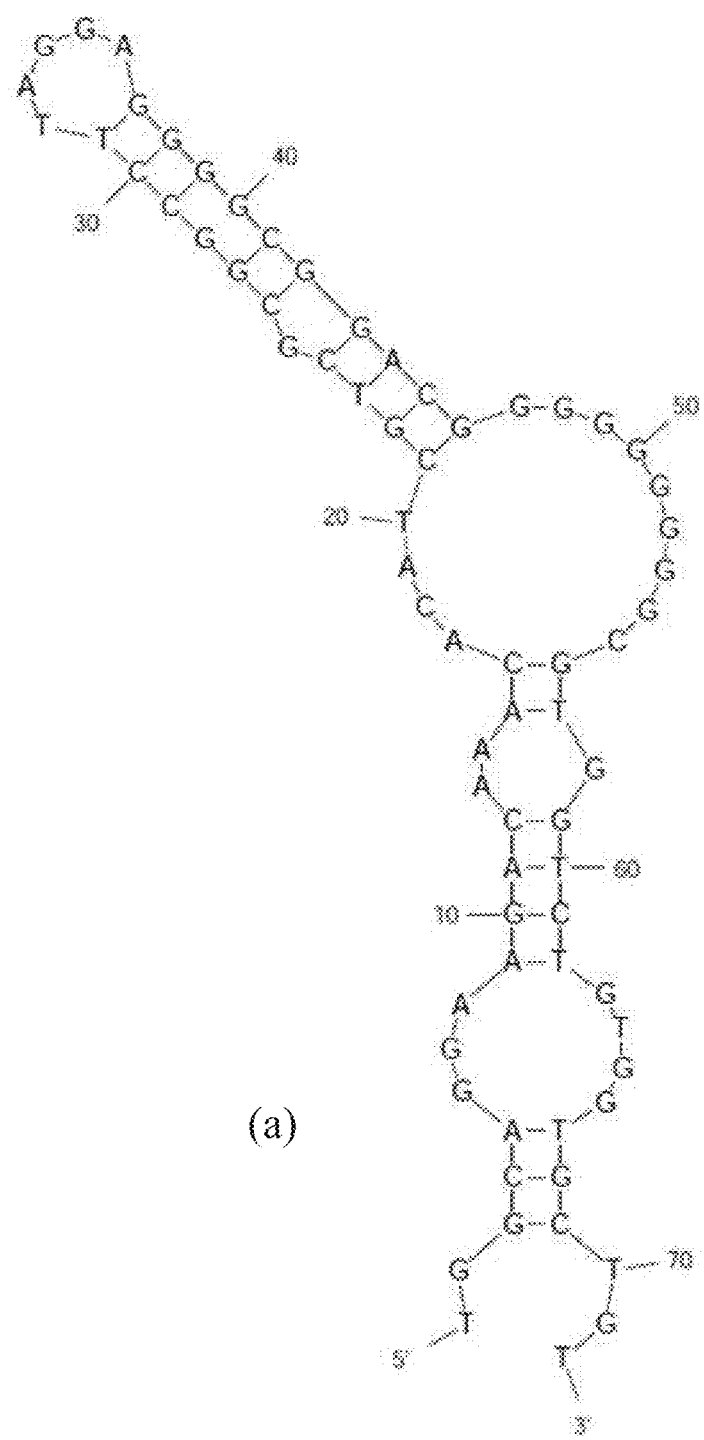
FIG. 3, the secondary structure of the hemoglobin A1c-specific aptamer of the present invention, wherein (a) is SEQ ID NO: 3; (b) is SEQ ID NO: 4.
Figure 3:
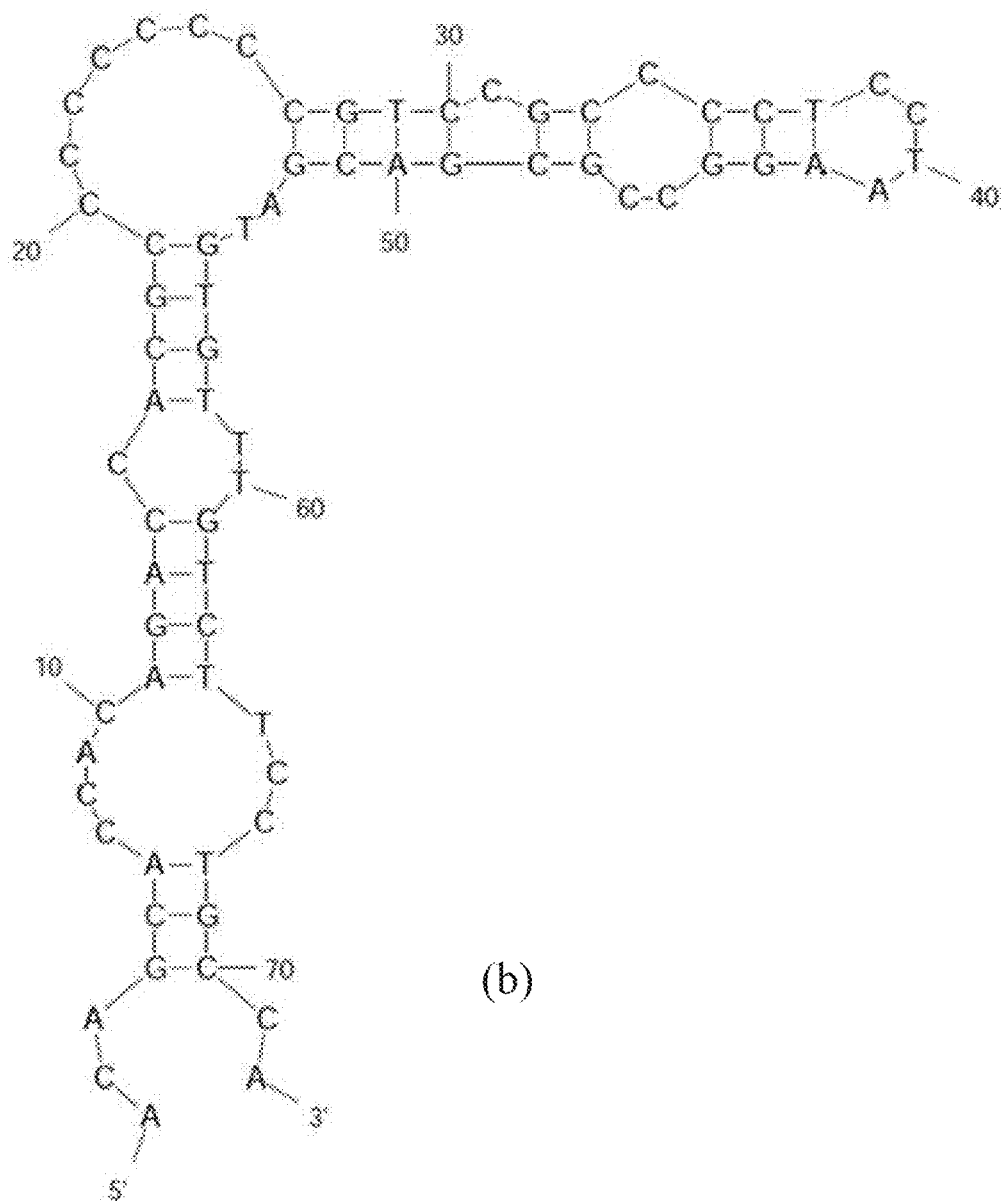

After the competitive analysis, the DNA molecules with the highest specific binding ability to hemoglobin A1c were selected for DNA sequencing. As a result, nucleic acid sequence: 5'-TGGCAGGAAGACAAACACATCGTCGCGGCCTTAGGAGGGGCG-GACGGGGGGGGGCGTGGTCTGTGGTGCTGT-3' (SEQ ID NO: 3) and nucleic acid sequence: 5'-ACAGCACCACA-GACCACGCCCCCCCCGTCCGCCCCTC-CTAAGGCCG-CGACGATGTGTTTGTCTTCCTGCCA-3' (SEQ ID NO: 4) were obtained. The secondary structures of SEQ ID NO: 3 and SEQ ID NO: 4 were further predicted using MFOLD and the results are shown in FIG. 3. The nucleic acid sequence of SEQ ID NO: 3 exhibits a lower free energy of −14.9 kcal/mol and comprises the nucleic acid sequence of SEQ ID NO: 1, which is a nucleic acid sequence of 40 nt in length. On the other hand, the nucleic acid sequence of SEQ ID NO: 4 exhibits a free energy of −11.47 kcal/mol and comprises the nucleic acid sequence of SEQ ID NO: 2.

Thus, the present invention provides a hemoglobin A1c-specific aptamer, which is, preferably, the nucleic acid sequence of SEQ ID NO: 3 or the nucleic acid sequence of SEQ ID NO: 4, wherein the nucleic acid sequence of SEQ ID NO: 3 comprises a nucleic acid sequence of SEQ ID NO: 1 for specific binding with hemoglobin A1c, a Forward primer (SEQ ID NO: 9) and a Reverse primer (SEQ ID NO: 10); the nucleic acid sequence of SEQ ID NO: 4 comprises a nucleic acid sequence of SEQ ID NO: 2 for specific binding with hemoglobin A1c, a Forward primer (SEQ ID NO: 11) and a Reverse primer (SEQ ID NO: 12).

EXAMPLE 2

Detection of Hemoglobin A1c using the Hemoglobin A1c-Specific Aptamer

The method used to detect hemoglobin A1c in the present invention is known as a Two-antibody assay and is performed using the above detection microfluidic chip. Firstly, blood and the magnetic bead conjugated with anti-HbA1c antibody were added to the reaction chamber of the microfluidic chip and were mixed by micromixer. After hemoglobin A1c in blood bound to the magnetic bead conjugated with HbA1c antibody, a magnetic field was applied and the unbound substances were washed away. Then, a luminescent agent-labeled HbA1c antibody, preferably acridinium ester-labeled HbA1c antibody, was added to the reaction chamber to allow reaction with the HbA1c captured to take place. Finally, $H_2O_2$ and NaOH were added and mixed, and the chemiluminescence signals were detected by luminometer.

Figure 4:
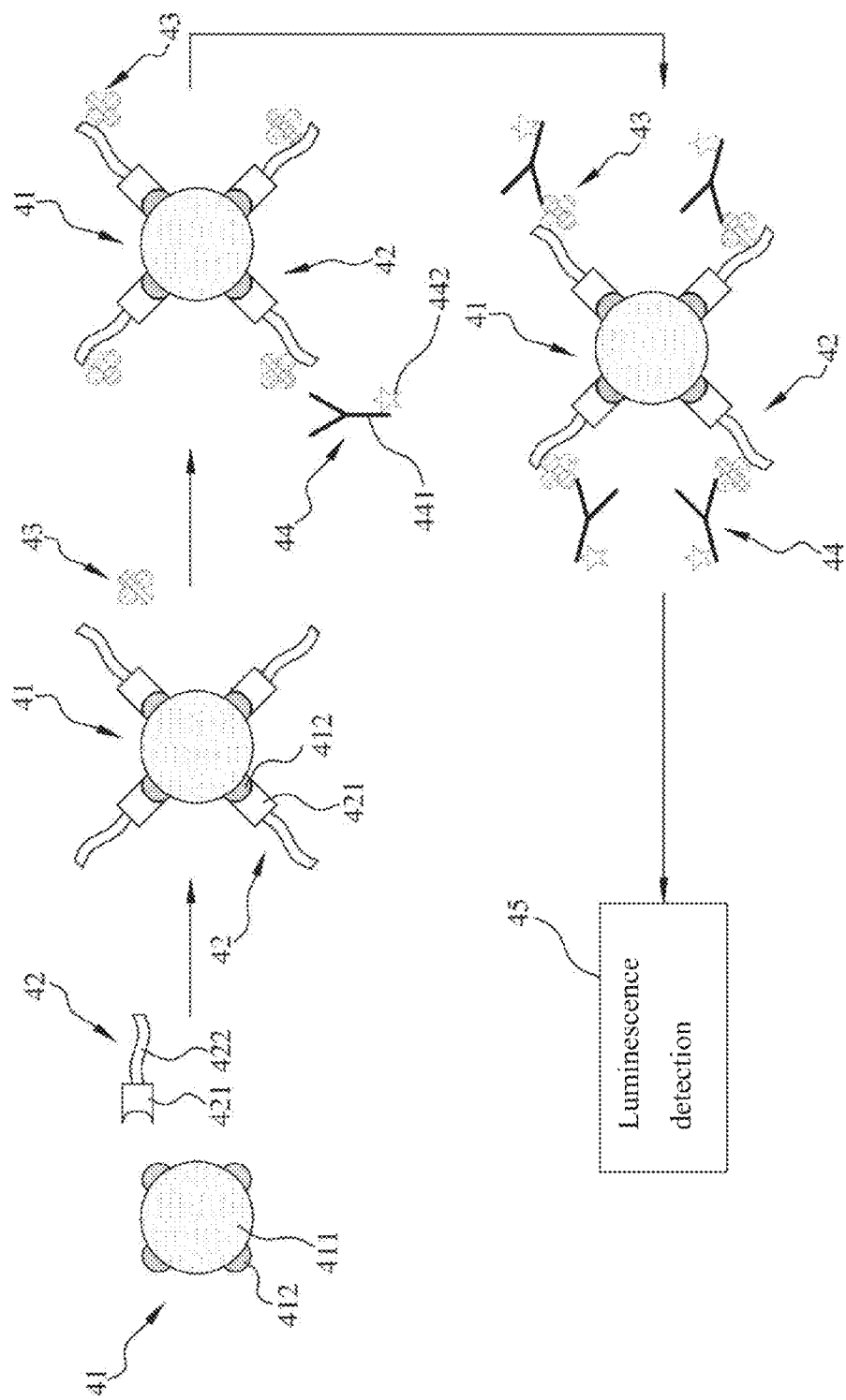
FIG. 4, flow chart for the detection of hemoglobin A1c in blood using the hemoglobin A1c-specific aptamer of the present invention.
Figure 5:
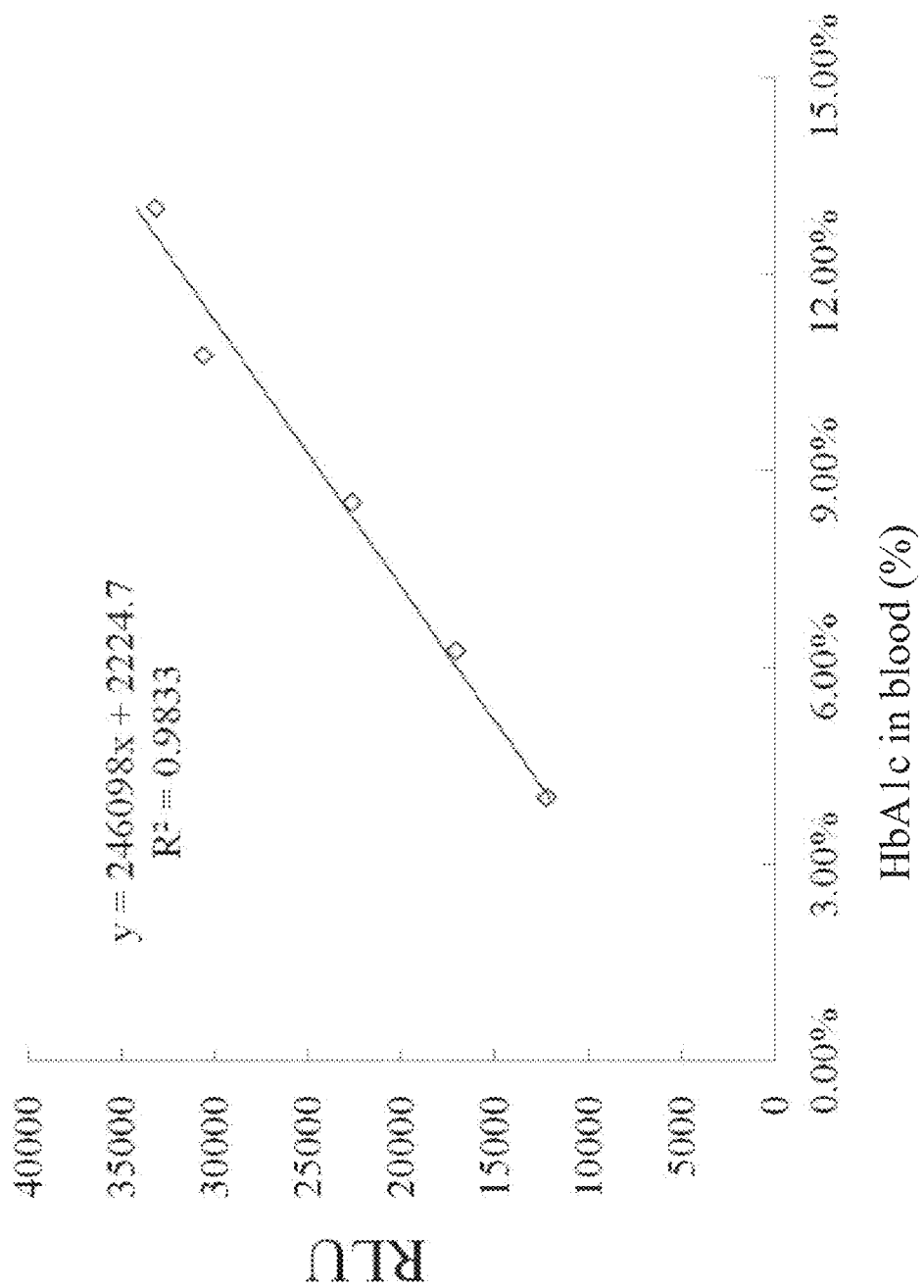
FIG. 5, the binding rate of SEQ ID NO: 3 to hemoglobin A1c; RLU is relative luminescence unit.
Figure 6:
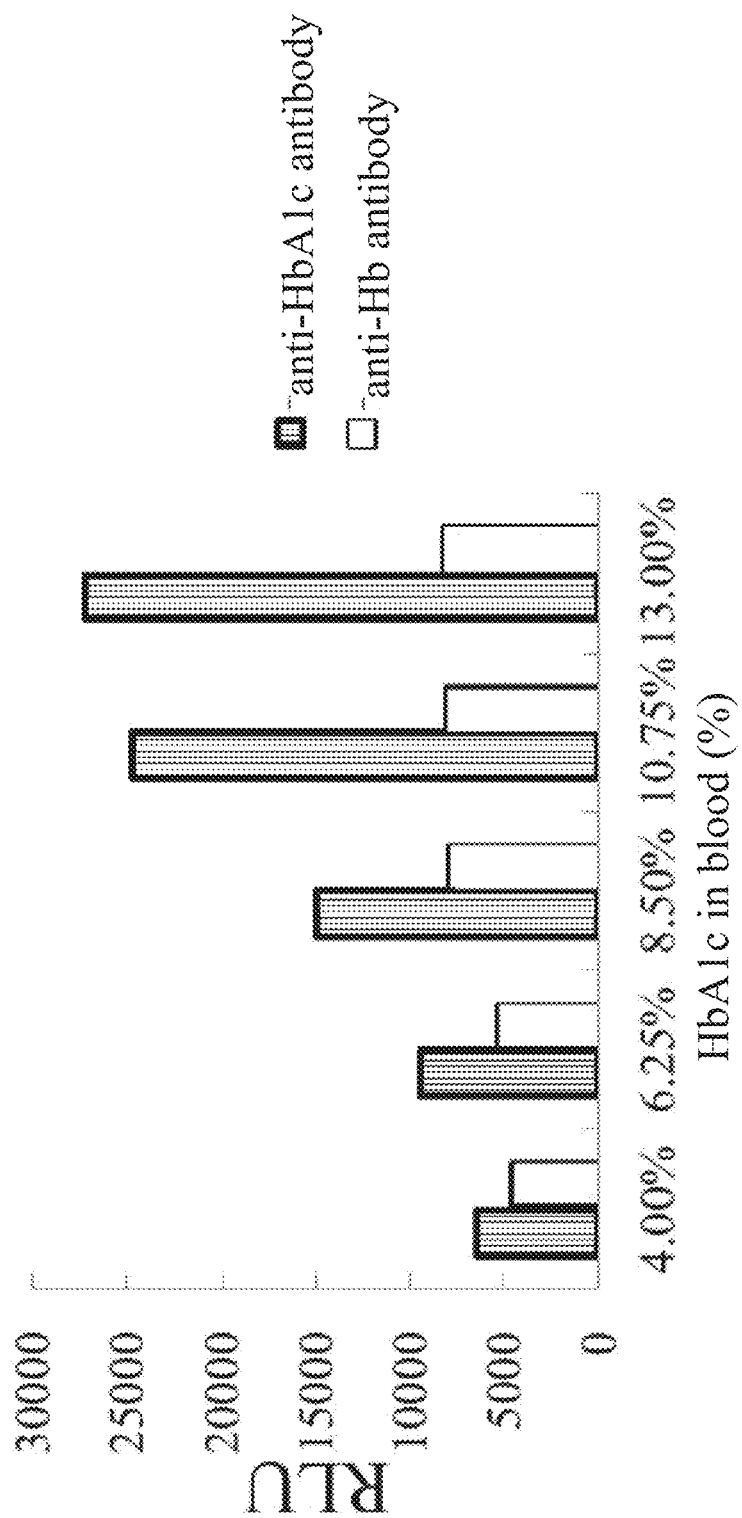
FIG. 6, the specificity of SEQ ID NO: 3 to hemoglobin A1c; RLU is relative luminescence unit.

Please refer to FIG. 4, the flow chart for the detection of hemoglobin A1c in blood using the hemoglobin A1c-specific aptamer of the present invention. Firstly, HbA1c-specific aptamer 422, preferably the nucleic acid sequence of SEQ ID NO: 3 with low free energy, was used. The 5' end of the aptamer 422 was labeled by biotin 421. The aptamer 422 was used to replace the anti-HbA1c antibody which conjugated with the magnetic bead in the above two-antibody assay. Streptavidin 412 was conjugated to the surface of the magnetic bead 411. The biotin-labeled aptamer 42 was further linked to the streptavidin-conjugated magnetic bead 41 and mixed with blood. The aptamer 422 of the present invention would bind to hemoglobin A1c 43 in blood. A magnetic filed was applied and the unbound substances were washed away. Then, an anti-HbA1c antibody 441 labeled with acridinium ester 422 was provided, and this acridinium ester-labeled anti-HbA1c antibody 44 was added. Finally, luminescence detection 45 was performed after the reaction. The result of the detection of HbA1c in blood is shown in FIG. 5, in which the HbA1c-specific aptamer of the present invention can bind to hemoglobin A1c in blood with a high slope ($R^2$=0.9833) indicating that the HbA1c-specific aptamer of the present invention exhibits high binding rate to hemoglobin A1c.

Besides, the chemiluminescence signal detected would reduce significantly if the acridinium ester-labeled anti-HbA1c antibody of the above detection process is replaced by acridinim ester-labeled anti-Hb antibody, indicating that the HbA1c-specific apatmer specifically binds to hemoglobin A1c but not hemoglobin.

EXAMPLE 3

Selection of Hemoglobin-Specific Aptamer

The present invention also utilize SELEX microfluidic chip to select hemoglobin-specific aptamer which can be used to substitute antibody as a biomarker for identifying hemoglobin in blood. The selection process of hemoglobin-specific aptamer is similar to Example 1, therefore, please refer to FIG. 1 for the flow chart for the selection of aptamer specific for target protein (hemoglobin A1c or hemoglobin) using the microfluidic chip of the present invention. Please note that the target protein of this embodiment is hemoglobin.

In this embodiment, the SELEX selection is a hemoglobin positive selection when hemoglobin-magnetic bead complex was used to bind with single strand DNA molecule, whereas the SELEX selection is a hemoglobin negative selection when BSA-magnetic bead complex was used. According the hemoglobin positive and hemoglobin negative selection of this embodiment, aptamer with high specificity to hemoglobin can be obtained.

Figure 7:
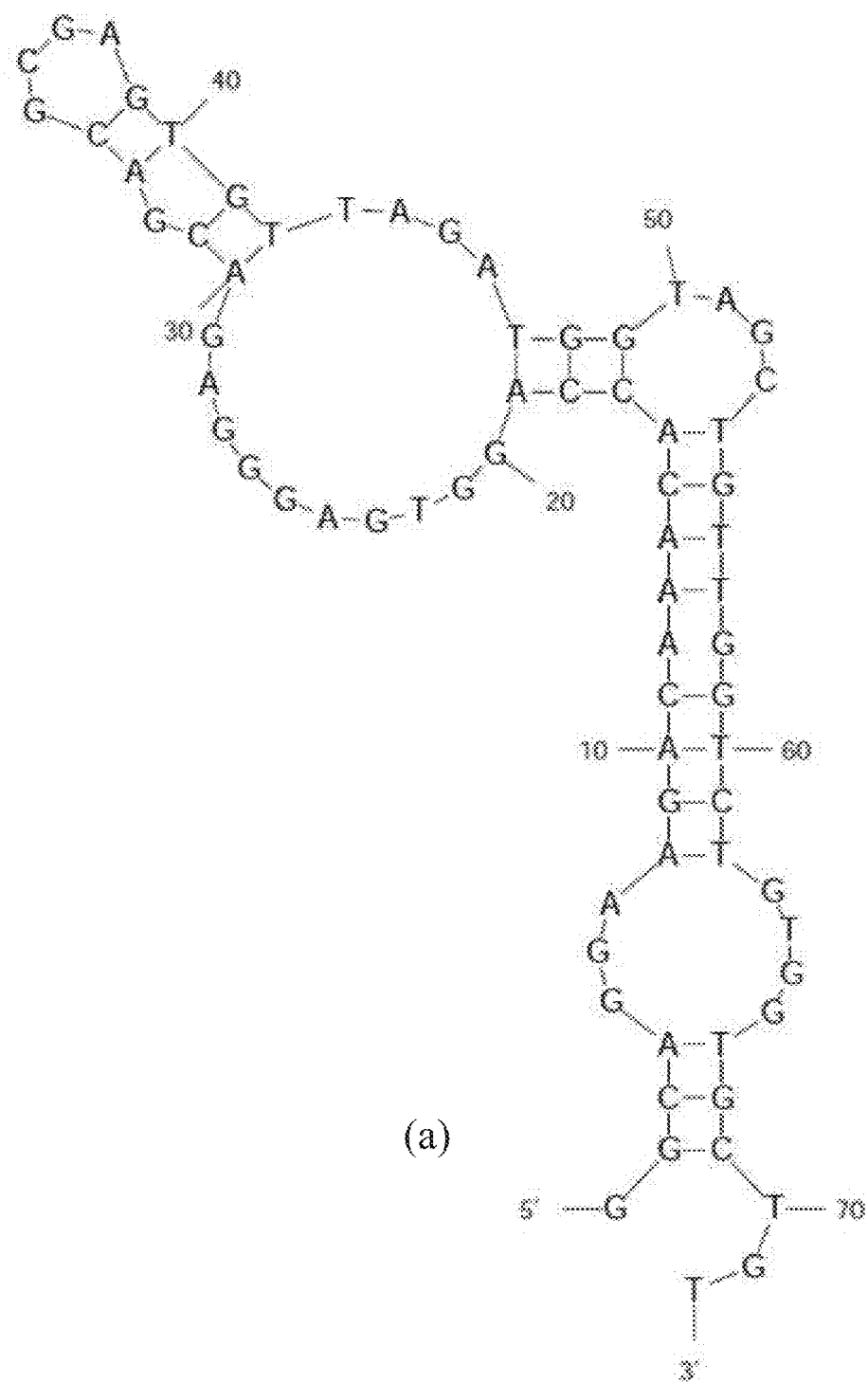
FIG. 7, illustration of the secondary structure of the hemoglobin-specific aptamer of the present invention, wherein (a) is SEQ ID NO: 7; (b) is SEQ ID NO: 8.
Figure 7:
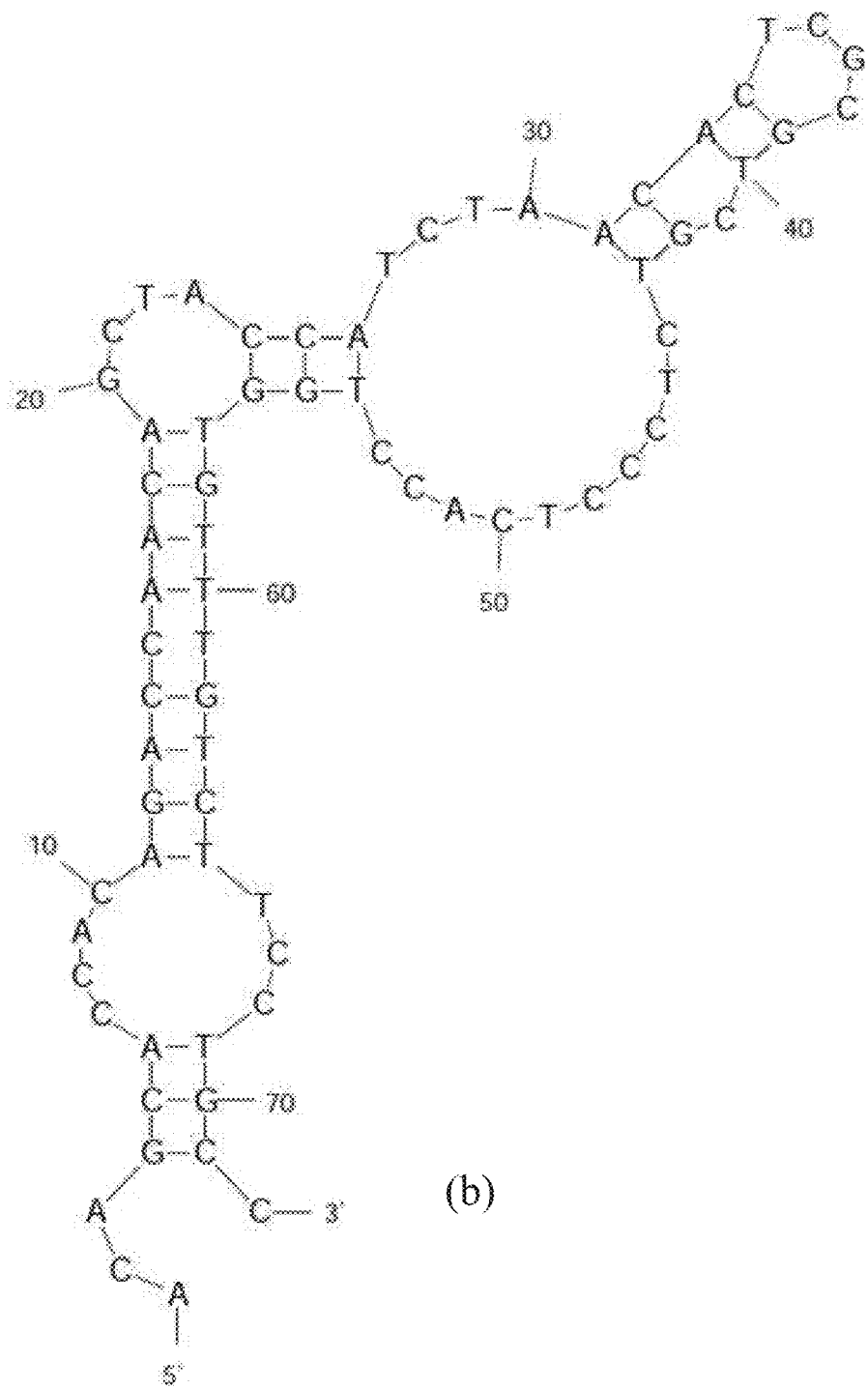

The single strand DNA molecules with high hemoglobin specificity selected in this embodiment were further underwent DNA sequencing. As a result, nucleic acid sequence: 5'-GGCAGGAAGACAAACACCAGGTGAGGGAGACG-ACGCGAGTGTTAGATGGTAGCTGTTG-GTCTGTGGTGCTGT-3' (SEQ ID NO: 7) and nucleic acid sequence: 5'-ACAGCACCACAGACCAACAGCTAC-CATC-TAACACTCGCGTCGTCTCCCTCACCTG-GTGTTTGTCTTCCTGCC-3' (SEQ ID NO: 8) were obtained. The secondary structures of SEQ ID NO: 7 and SEQ ID NO: 8 were predicted using MFOLD and the results are shown in FIG. 7, wherein (a) shows that the nucleic acid sequence of SEQ ID NO: 7 exhibits a lower free energy of −9.67 kcal/mol and comprises a nucleic acid sequence of SEQ ID NO: 5, which is a nucleic acid sequence of 40 nt in length. On the other hand, (b) shows that the nucleic acid sequence of SEQ ID NO: 8 exhibits free energy of −6.37 kcal/mol and comprises the nucleic acid sequence of SEQ ID NO: 6, which is a nucleic acid sequence of 40 nt in length.

Thus, the present invention provides a hemoglobin-specific aptamer, which is, preferably, the nucleic acid sequence of SEQ ID NO: 7 or the nucleic acid sequence of SEQ ID NO: 8, wherein the nucleic acid sequence of SEQ ID NO: 7 comprises a nucleic acid sequence of SEQ ID NO: 5 for specific binding with hemoglobin , a Forward primer (SEQ ID NO: 13) and a Reverse primer (SEQ ID NO: 14); the nucleic acid sequence of SEQ ID NO: 8 comprises a nucleic acid sequence of SEQ ID NO: 6 for specific binding with hemoglobin , a Forward primer (SEQ ID NO: 15) and a Reverse primer (SEQ ID NO: 16).

EXAMPLE 4

Detection of Hemoglobin using the Hemoglobin-Specific Aptamer

Figure 8:
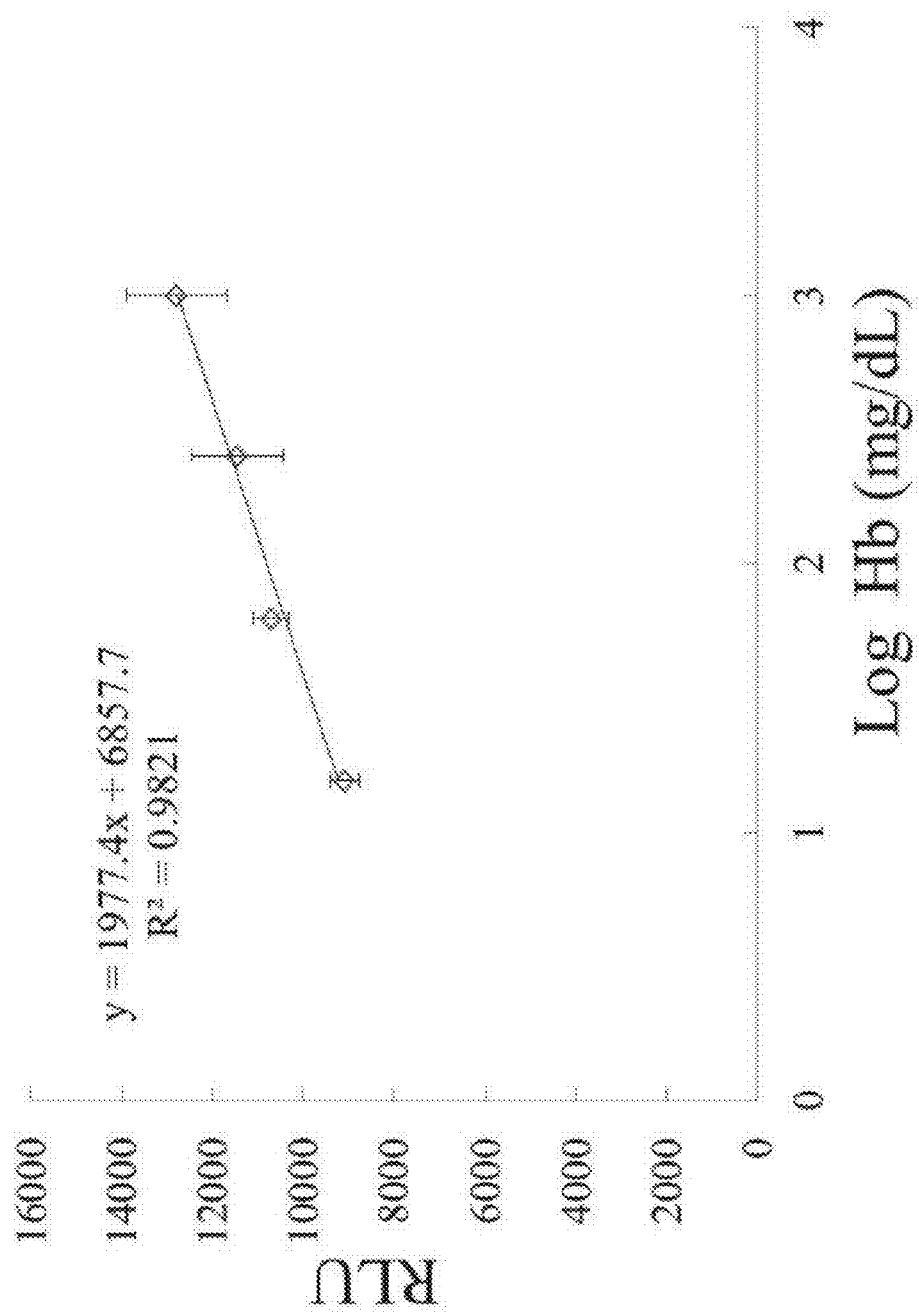
FIG. 8, the binding rate of SEQ ID NO: 7 to hemoglobin; RLU is relative luminescence unit.

The detection of this embodiment is also a two-antibody assay; therefore, please refer to Example 2 for the detection process. In this embodiment, the nucleic acid sequence of SEQ ID NO: 7 with lower free energy was used as the aptamer. The aptamer was labeled by biotin and was used to replace the anti-Hb antibody in the two-antibody assay. The surface of the magnetic bead used was also conjugated with streptavidin. Upon mixing with blood, the hemoglobin-specific aptamer would bind to hemoglobin in blood. After a magnetic field was applied and the unbound substances were washed away, an acridinium ester-labeled anti-Hb antibody was added. The acridinium ester-labeled anti-Hb antibody produces chemiluminescense, thus, can be detected using luminometer. The result of the detection of hemoglobin is shown in FIG. 8, in which the Hb-specific aptamer of the present invention can bind to hemoglobin in blood with a high slope ($R^2$=0.9821) indicating that the Hb-specific aptamer of the present invention exhibits high binding rate to hemoglobin.

In conclusion, the aptamer of the present invention exhibits high specificity and high binding activity to hemoglobin A1c or hemoglobin. The aptamer has low molecular weight and low free energy. The aptamer also has advantages such as reusable and easily to be attached to other molecules; hence, when comparing to antibody, the aptamer can not only overcome the drawbacks caused by animal production but also be easily synthesized as well as reserve the accuracy of production. Thus, the aptamer of the present invention is suitable for detecting hemoglobin A1c and/or hemoglobin in blood.

The HbA1c-specific aptamer, Hb-specific aptamer, microfluidic chip for detecting the presence of hemoglobin A1c and/or hemoglobin in blood, and the method for detecting the presence of hemoglobin A1c and/or hemoglobin in blood provided in the present invention are applicable and valuable to the industry. Those embodiments above are better results, and should not, however, be considered to limit the scope of the invention, it is contemplated that modifications will readily occur to those skilled in the art, which modifications will be within the spirit of the invention and scope of the appended claims.

What is claimed is:

1. An aptamer that specifically binds to hemoglobin A1c, wherein the aptamer is a nucleic acid molecule consisting essentially of:
the nucleic acid sequence of SEQ ID NO: 1.

2. The aptamer of claim 1, wherein when the aptamer consists essentially of the nucleic acid sequence of SEQ ID NO: 1, the aptamer further comprises a forward primer of a nucleic acid sequence of SEQ ID NO: 9, and a reverse primer of a nucleic acid sequence of SEQ ID NO: 10.

3. An aptamer that specifically binds to hemoglobin, wherein the aptamer is a nucleic acid molecule consisting essentially of:
the nucleic acid sequence of SEQ ID NO: 5.

4. The aptamer of claim 3, wherein when the aptamer consists essentially of the nucleic acid sequence of SEQ ID NO: 5, the aptamer further comprises a forward primer of a nucleic acid sequence of SEQ ID NO: 13, and a reverse primer of a nucleic acid sequence of SEQ ID NO: 14.

5. A microfluidic chip for detecting the presence of hemoglobin A1c or hemoglobin in blood, comprising the aptamer of SEQ ID. NO: 3 or SEQ ID. NO: 7.

6. A method for detecting the presence and/or amount of hemoglobin A1c and/or hemoglobin, comprising the steps of:
(a) obtaining a sample of bodily fluid from a subject;
(b) contacting the sample with at least one aptamer comprising a hemoglobin A1c-specific nucleic acid sequence or a hemoglobin-specific nucleic acid sequence to allow the aptamer to bind to hemoglobin A1c and/or hemoglobin in the sample, wherein the hemoglobin A1c-specific nucleic acid sequence or the hemoglobin-specific nucleic acid sequence is selected from: the group consisting of a nucleic acid sequence of: SEQ ID NO:1 and SEQ ID NO: 5;and
(c) detecting the hemoglobin A1c and/or hemoglobin bound to the aptamer of step (b), whereby presence and/or amount of hemoglobin A1c and/or hemoglobin in the sample is determined,
wherein, if step (c) is to determine the presence and/or amount of hemoglobin A1c in the sample, an aptamer of SEQ ID NO: 3 comprising the hemoglobin A1c-specific nucleic acid sequence of SEQ ID NO: 1 is selected; if step (c) is to determine the presence and/or amount of hemoglobin in the sample, an aptamer of SEQ ID NO: 7 comprising the hemoglobin-specific nucleic acid sequence of SEQ ID NO: 5 is selected.

7. The method of claim 6, wherein the sample is a blood sample.

8. The method of claim 6, wherein the determination of the presence and/or amount of hemoglobin A1c and/or hemoglobin in step (c) further comprises binding the hemoglobin A1c and/or hemoglobin with a light emitting reagent.

9. The method of claim 8, wherein the light emitting reagent emits luminescence, fluorescence, visible light, or ultraviolet light.

* * * * *